(12) United States Patent
Klem et al.

(10) Patent No.: US 10,611,391 B1
(45) Date of Patent: Apr. 7, 2020

(54) MOBILE SUPPORT AND STORAGE SYSTEM FOR A MEDICAL DEVICE

(71) Applicant: Corindus, Inc., Waltham, MA (US)

(72) Inventors: Eric Klem, Lexington, MA (US); Gordon Row, Groton, MA (US); Genevieve R. K. Laing, Medford, MA (US); Christopher O. Evans, Amherst, NH (US); Anthony Clegg Parker, New Ipswich, WI (US)

(73) Assignee: CORINDUS, INC., Waltham, MA (US)

( * ) Notice: Subject to any disclaimer, the term of this patent is extended or adjusted under 35 U.S.C. 154(b) by 0 days.

(21) Appl. No.: 16/152,811

(22) Filed: Oct. 5, 2018

(51) Int. Cl.
| | | |
|---|---|---|
| *A61G 13/10* | (2006.01) | |
| *B62B 3/04* | (2006.01) | |
| *A61G 7/05* | (2006.01) | |
| *A61G 12/00* | (2006.01) | |

(52) U.S. Cl.
CPC .............. *B62B 3/04* (2013.01); *A61G 7/0524* (2016.11); *A61G 13/101* (2013.01); *A61G 12/001* (2013.01); *B62B 2202/00* (2013.01); *B62B 2203/24* (2013.01)

(58) Field of Classification Search
CPC ...... B62B 3/04; A61G 7/0524; A61G 13/101; A61G 12/001
See application file for complete search history.

(56) References Cited

U.S. PATENT DOCUMENTS

| | | |
|---|---|---|
| 3,304,609 A | 2/1967 | Horowitz et al. |
| 3,922,996 A | 12/1975 | Meyer |
| 4,199,294 A | 4/1980 | Streck et al. |
| 4,637,494 A | 1/1987 | Iida et al. |

(Continued)

FOREIGN PATENT DOCUMENTS

WO     2003015428 A9     12/2003

OTHER PUBLICATIONS

International Search Report and Written Opinion for PCT/US2019/054446; dated Feb. 7, 2020; 11 pages.

*Primary Examiner* — Brian L Swenson
(74) *Attorney, Agent, or Firm* — Rathe Lindenbaum LLP

(57) ABSTRACT

A mobile support system for a medical device having an arm with a base includes a body comprising a housing having a top surface, a first end and a second end and a carriage positioned within the housing. The mobile support system further includes a mechanism coupled to the carriage and configured to cause movement of the carriage, a set of wheels coupled to the housing and a support arm coupled to the carriage and extending vertically upward from the top surface of the housing. The support arm is configured to support the arm of the medical device. The mobile support system also includes a mounting block coupled to the carriage proximate to the support arm, the mounting block configured to couple with the base of the arm of the medical device, a first rail detect guide located on the top surface at the second end of the housing and a second rail detect guide located on the top surface at the second end of the housing. The first rail detect guide and the second rail detect guide are configured to unlock the mechanism used to cause movement of the carriage when contact is made between the first rail detect guide and the second rail detect guide and a surface.

25 Claims, 15 Drawing Sheets

(56) References Cited

U.S. PATENT DOCUMENTS

| | | | |
|---|---|---|---|
| 4,917,619 A | 4/1990 | Nishiwaki | |
| 5,696,574 A | 12/1997 | Schwaegerle | |
| 5,907,487 A | 5/1999 | Rosenberg et al. | |
| 6,999,849 B2 | 2/2006 | Bridges | |
| 7,278,615 B2* | 10/2007 | Schubert | A61G 12/001 |
| | | | 211/207 |
| 8,333,692 B2 | 12/2012 | Masaki | |
| 8,348,287 B1* | 1/2013 | Smith | B62B 3/04 |
| | | | 280/47.34 |
| 8,390,438 B2 | 3/2013 | Olson et al. | |
| 8,881,359 B2 | 11/2014 | Matsuoka et al. | |
| 8,888,083 B2 | 11/2014 | Hosaka | |
| 2001/0035702 A1 | 11/2001 | Murphy et al. | |
| 2003/0093862 A1* | 5/2003 | Hanson | A61G 7/005 |
| | | | 5/613 |
| 2005/0206107 A1* | 9/2005 | Schubert | A61G 12/001 |
| | | | 280/79.11 |
| 2005/0278851 A1* | 12/2005 | DeMayo | A61G 13/10 |
| | | | 5/624 |
| 2006/0163829 A1 | 7/2006 | Livengood et al. | |
| 2009/0248042 A1 | 10/2009 | Kirschenman | |
| 2011/0015484 A1 | 1/2011 | Alvarez et al. | |
| 2011/0247903 A1 | 10/2011 | Boukhny et al. | |
| 2012/0224673 A1* | 9/2012 | Barker | A61B 6/4405 |
| | | | 378/198 |
| 2014/0205371 A1* | 7/2014 | Bally | A61G 12/008 |
| | | | 403/327 |
| 2014/0215718 A1* | 8/2014 | Wootton | A61G 13/0036 |
| | | | 5/621 |
| 2015/0190265 A1* | 7/2015 | Kreuzer | A61F 5/048 |
| | | | 602/33 |
| 2015/0223892 A1 | 8/2015 | Miller et al. | |
| 2019/0298597 A1* | 10/2019 | Ito | A61G 13/1295 |

\* cited by examiner

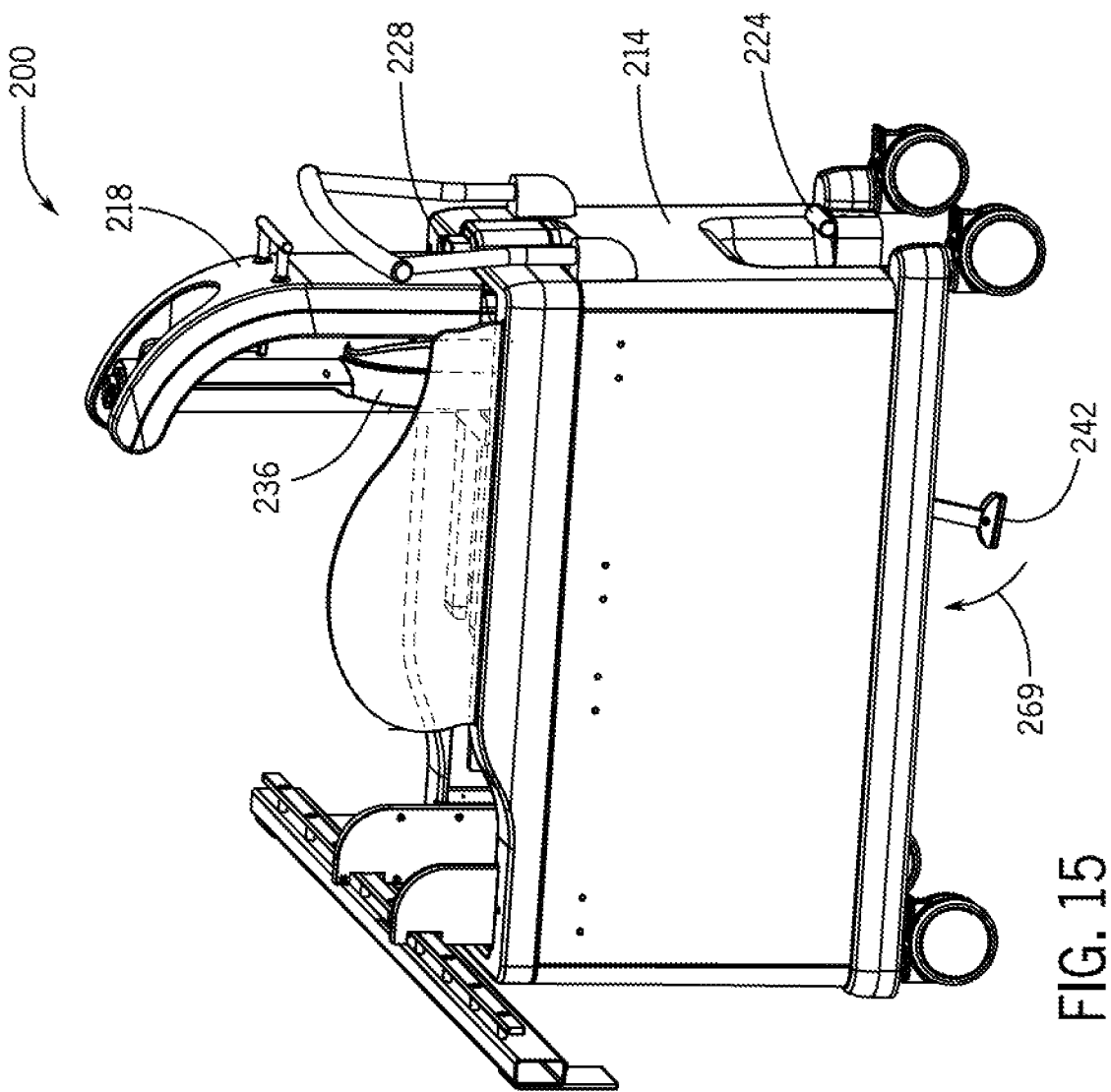

MOBILE SUPPORT AND STORAGE SYSTEM FOR A MEDICAL DEVICE

FIELD OF THE INVENTION

The present invention relates generally to the field of medical devices and more particularly to a mobile support and storage system for a medical device.

BACKGROUND OF THE INVENTION

Medical beds or tables used in hospitals, clinics, doctor offices or other medical environments may include a rail operatively secured to the bed for supporting various medical devices. There may be circumstances where it is desirable to remove the medical device from the table between procedures. However, such devices may be heavy and manually installing and removing the medical devices can be difficult.

It would be desirable to provide a mobile support and storage system that is configured to facilitate installation and removal of a medical device with respect to a rail on a medical bed or table and that is also configured to transport and store the medical device.

SUMMARY OF THE INVENTION

In accordance with an embodiment, a mobile support system for a medical device having an arm with a base, includes a body comprising a housing having a top surface, a first end and a second end and a carriage positioned within the housing, a mechanism coupled to the carriage and configured to cause movement of the carriage, a set of wheels coupled to the housing, a support arm coupled to the carriage and extending vertically upward from the top surface of the housing, the support arm configured to support the arm of the medical device, a mounting block coupled to the carriage proximate to the support arm, the mounting block configured to couple with the base of the arm of the medical device, a first rail detect guide located on the top surface at the second end of the housing and a second rail detect guide located on the top surface at the second end of the housing, wherein the first rail detect guide and the second rail detect guide are configured to unlock the mechanism used to cause movement of the carriage when contact is made between the first rail detect guide and the second rail detect guide and a surface.

In accordance with another embodiment, a mobile support system for a medical device having an arm with a base, includes a body comprising a housing having a top surface and a carriage positioned within the housing, a mechanism coupled to the carriage and configured to cause movement of the carriage, a set of wheels coupled to the housing, a floor brake coupled to the housing, the floor brake configured to be actuated in response to movement of the carriage, a support arm coupled to the carriage and extending vertically upward from the top surface of the housing, the support arm configured to support the arm of the medical device and a mounting block coupled to the carriage proximate to the support arm, the mounting block configured to couple with the base of the arm of the medical device.

In accordance with another embodiment, a mobile support system includes a medical device having an arm with a base, the base comprising a rail detect lever configured to be actuated when contact is made between the rail detect lever and a surface, a body comprising a housing and a carriage positioned within the housing, a support arm coupled to the carriage and extending vertically upward from the housing, the support arm configured to support the arm of the medical device and a mounting block coupled to the carriage proximate to the support arm, the mounting block configured to couple with the base of the arm of the medical device.

In accordance with another embodiment, a mobile support system includes a medical device having an arm with a base, the base comprising a brake and a brake release coupled to the brake, a body comprising a housing and a carriage positioned within the housing, a support arm coupled to the carriage and extending vertically upward from the housing, the support arm configured to support the arm of the medical device and a mounting block coupled to the carriage proximate to the support arm, the mounting block configured to couple with the base of the arm of the medical device, the mounting block configured to actuate the brake release when the mounting block engages the base of the arm.

In accordance with another embodiment, a mobile support system includes a medical device having an arm with a base, the base includes a first roller, a first roller shaft coupled to the first roller, a first locking mechanism coupled to the first roller shaft, a second roller, a second roller shaft coupled to the second roller and a second locking mechanism coupled to the second roller shaft. The mobile support system further includes a body comprising a housing and a carriage positioned within the housing, a support arm coupled to the carriage and extending vertically upward from the housing, the support arm configured to support the arm of the medical device and a mounting block coupled to the carriage proximate to the support arm, the mounting block configured to couple with the base of the arm of the medical device, the mounting block comprising a set of pins configured to couple with the first roller shaft and the second roller shaft, wherein the first locking mechanism and the second locking mechanism are configured to lock the first roller shaft and the second roller shaft, respectively, when the set of pins of the mounting block are disengaged from the first roller shaft and the second roller shaft.

BRIEF DESCRIPTION OF THE DRAWINGS

This application will become more fully understood from the following detailed description, taken in conjunction with the accompanying figures, wherein like reference numerals refer to like elements in which:

FIG. 15 is a perspective view of a mobile support system in a first position in accordance with an embodiment.

DETAILED DESCRIPTION OF THE PREFERRED EMBODIMENTS

In the following description, the vertical direction is the direction parallel to the direction of gravity and the horizontal direction is a direction generally perpendicular to the direction of gravity. The term upward will be a vertical direction opposite the direction of the force of gravity and the term downward will be a vertical direction in the direction of gravity.

Figure 1:
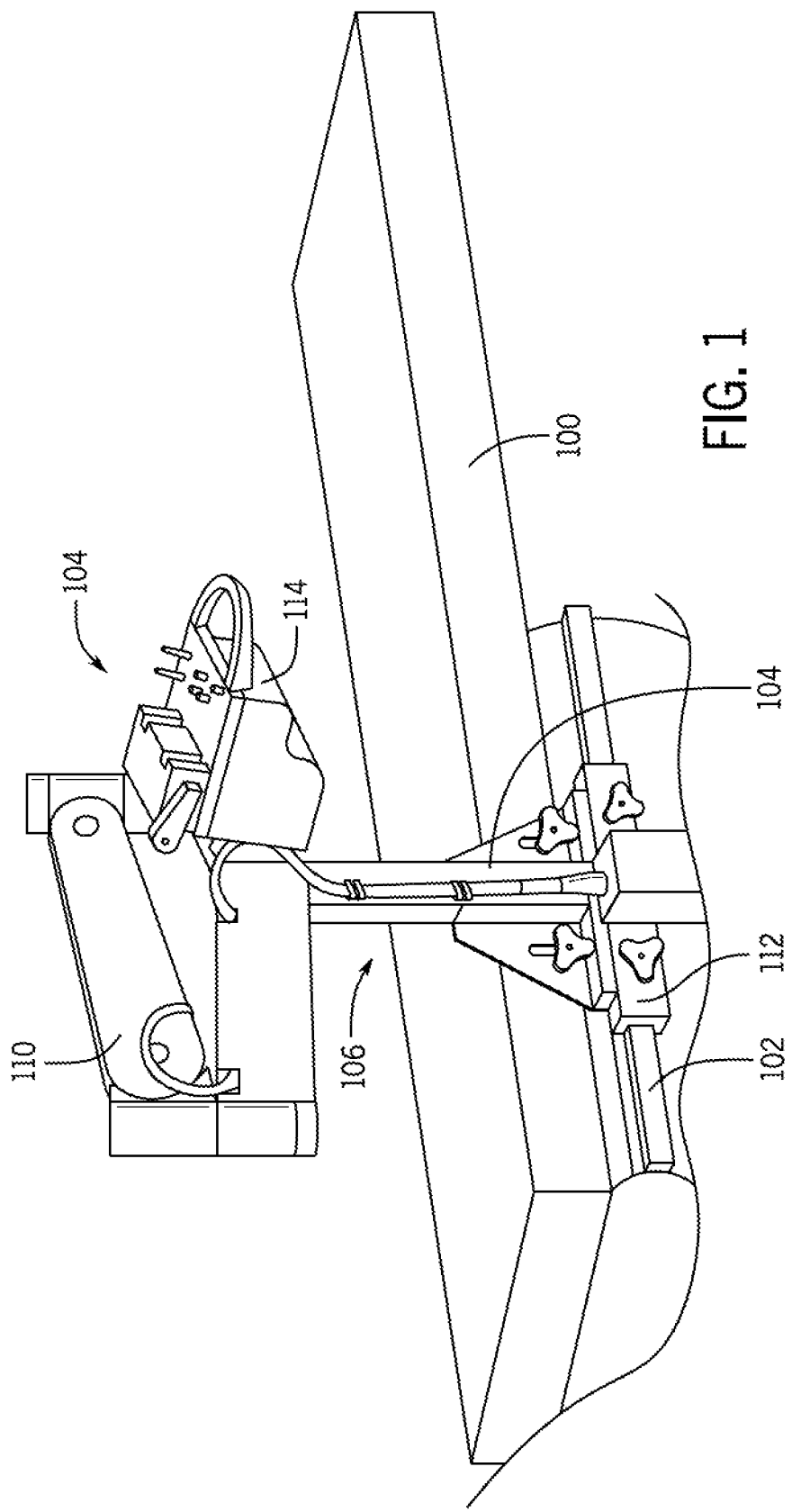
FIG. 1 is a schematic diagram of an exemplary medical bed or table with a medical device mounted to the medical bed or table in accordance with an embodiment.

FIG. 1 is a schematic diagram of an exemplary medical bed or table with a medical device mounted to the medical bed or table in accordance with an embodiment. In FIG. 1, a medical bed or table 100 includes a rail 102. A medical device 104 may be mounted to the table 100 using the rail 102. The medical device 104 includes an arm 106 that has a lower portion 108 and is used to support an instrument or system used in a medical procedure. In an embodiment, the arm 106 may include an articulated upper portion 110. The arm 106 also includes a base 112 that is configured to mount and secure the medical device 104 to the rail 102. The instrument or system supported by the arm 106 may be, for example, a robotic catheter system, an IV pole, a monitor, a contrast solution injector, etc. In FIG. 1, an exemplary robotic catheter system 114 is shown attached to the arm 106.

Figure 2:
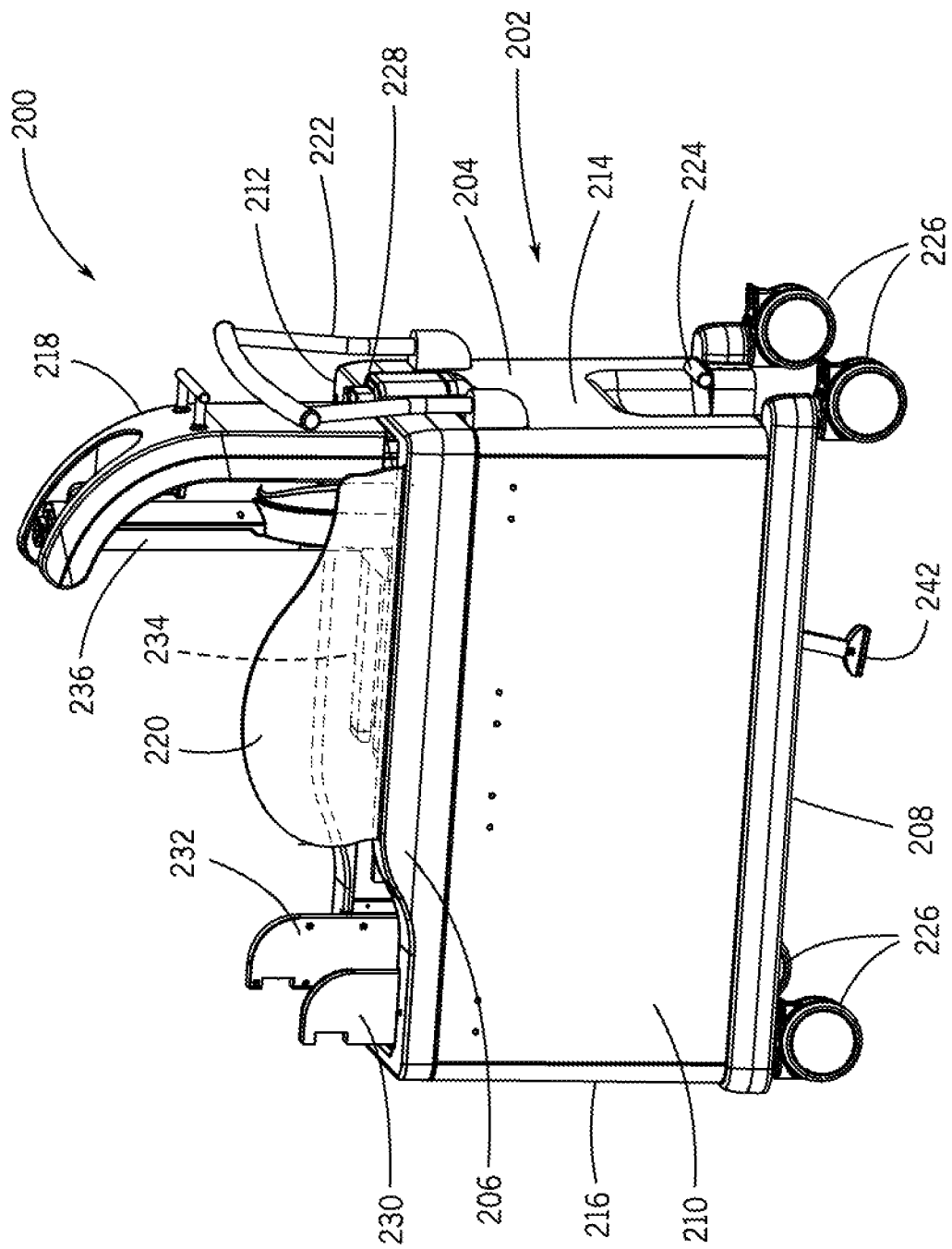
FIG. 2 is a perspective view of a mobile support system in a first position in accordance with an embodiment.
Figure 3:
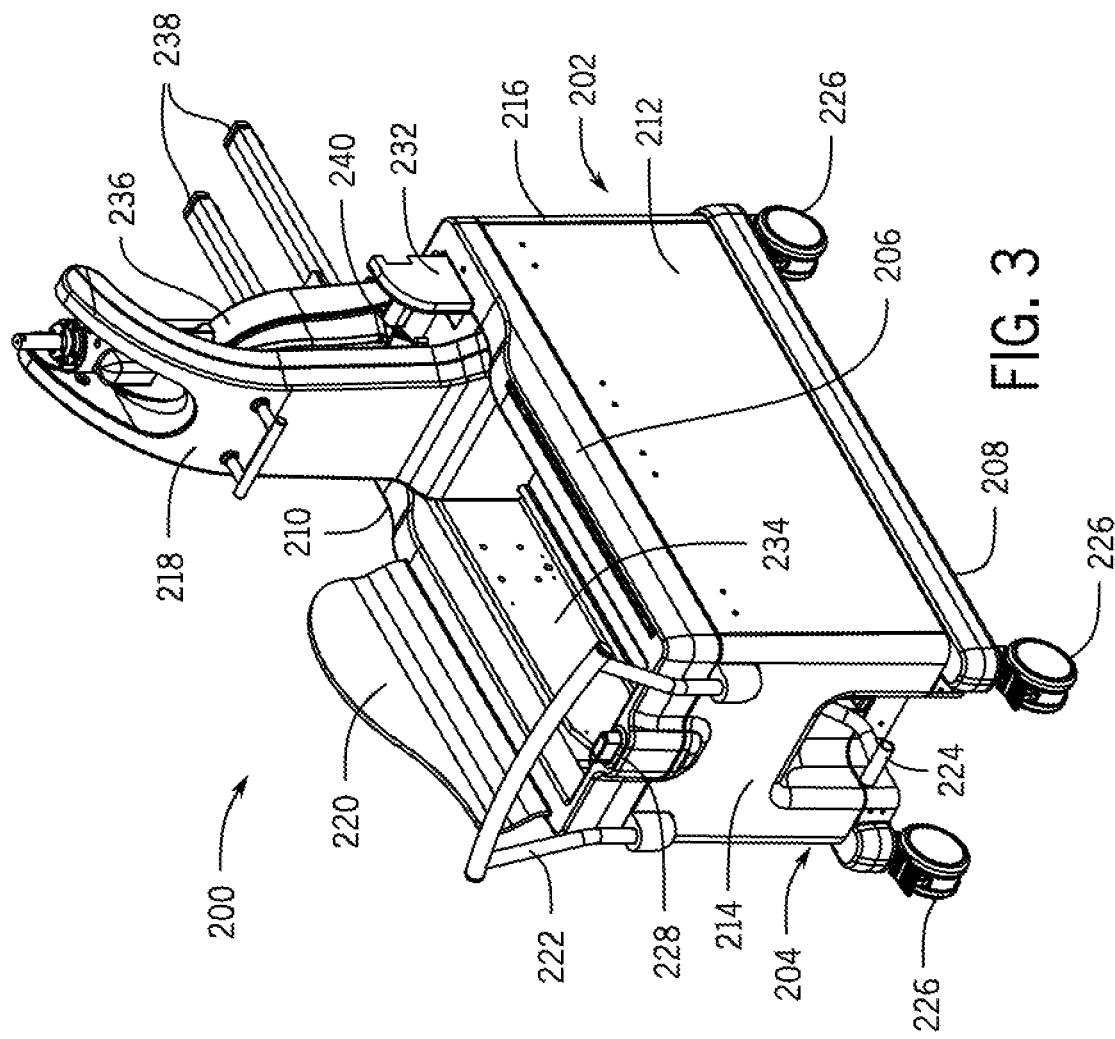
FIG. 3 is a perspective view of a mobile support system in a second position in accordance with an embodiment.

When the medical device 104 is not mounted to the table 100, the medical device 104 may be transported (to and from the table 100) and stored using a mobile support as described below with respect to FIGS. 2-15. The mobile support may also be used to install and remove the medical device 104 from the table 100. FIG. 2 is a perspective view of a mobile support system in a first position in accordance with an embodiment and FIG. 3 is a perspective view of a mobile support system in a second position in accordance with an embodiment. Referring to FIGS. 2 and 3, a mobile support 200 (e.g., a cart) includes a body 202 having a housing 204. The housing 204 includes a top surface 206, a bottom surface 208, a first side 210, a second side 212, a first end 214 and a second end 216. While a rectangular or cube shaped housing is shown, in other embodiments, the housing of the mobile support system 200 may have other shapes such as a cylinder and the housing may be a closed or open frame. A set of wheels 226 are attached to the bottom surface 208 of the housing 204. A floor brake 242 is also positioned on the bottom surface and is configured to be in a raised position when the mobile support 200 is used to transport and store the medical device and in a lowered position when the mobile support 200 is used to install the medical device on the rail of a bed or table and to remove the medical device from the rail of a bed or table as discussed further below.

Figure 4:
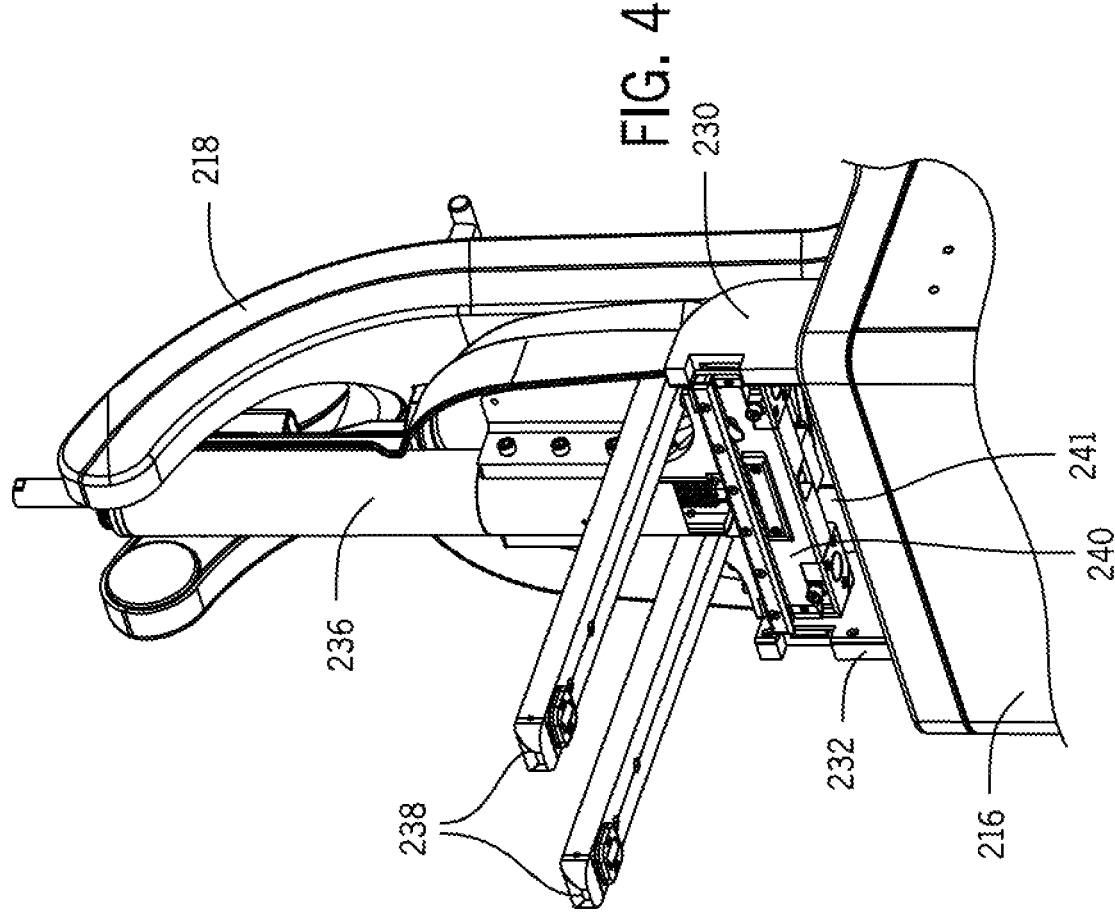
FIG. 4 is a perspective front view of a portion of a mobile support system in accordance with an embodiment.

The first end 214 of the housing includes a handle 222, a foot pedal 224 and a button 228. A support arm 218 is positioned in a carriage 234 inside the housing 204. In FIG. 2, the support arm 218 is located in a first position proximate the first end 214 of the housing 204. The first position shown in FIG. 2 may be used when the medical device is not in use and is being stored. In FIG. 3, the support arm 218 is located at a second position proximate the second end 216 of the housing 204. The second position shown in FIG. 3, may be used when the mobile support 200 is being used to install the medical device on or remove the medical device from the bed or table. A lower portion 236 of an arm of a medical device (e.g., lower portion 108 of arm 106 shown in FIG. 1) may be positioned in and adjacent to the support arm 218. For clarity, the remainder of the medical device (e.g., articulated portion 110 and instrument 114 shown in FIG. 1) is not shown. The lower portion 236 of the arm is removably attached to the support arm 218 (and the mobile support 200). For example, the support arm 218 may include a mounting block 241 (shown in FIG. 4) at a lower end of the support arm 218 proximate the top surface 206 of the housing and the carriage 234. Referring to FIG. 4, the lower portion 236 of the arm of the medical device includes a base 240 that is configured to engage the mounting block 241 when the medical device is mounted on the cart. In embodiments described below, the base 240 and mounting block 241 interface vertically. The base 240 is also configured to engage the rail of a bed or table when the medical device is mounted to the bed or table. The lower portion 236 of the arm also includes a set of feet 238 that may be located on top of the bed or table and under, for example, a mattress when the medical device is mounted and secured to the bed or table. The feet 238 may be used to apply load directly onto the table surface in addition to a rail on the table.

In FIG. 2, a side guide 220 is shown positioned along the top surface between the first end 214 and the second end 216 proximate to the first side 210 of the housing. In another embodiment, a side guide 220 may also be positioned along the top surface between the first end 214 and the second end 216 proximate to the second side 212. The side guide(s) 220 constrain and limit the range of motion of the support arm 218 and the arm 236 as they are moved from the first end 214 to the second end 216 of the housing 204 within the carriage 234. Limiting the range of motion of the support arm 218 and the arm 236 may result in increased stability of the mobile support system 200. A first rail detect guide 230 and a second rail detect guide 232 are located along the top surface proximate to the second end 216 of the housing. The first 230 and second 232 rail detect guide are configured to determine if the mobile support 200 and the arm 236 are in the correct position in relation to the rail of the bed or table for installation or removal of the medical device as described further below.

Figure 5:
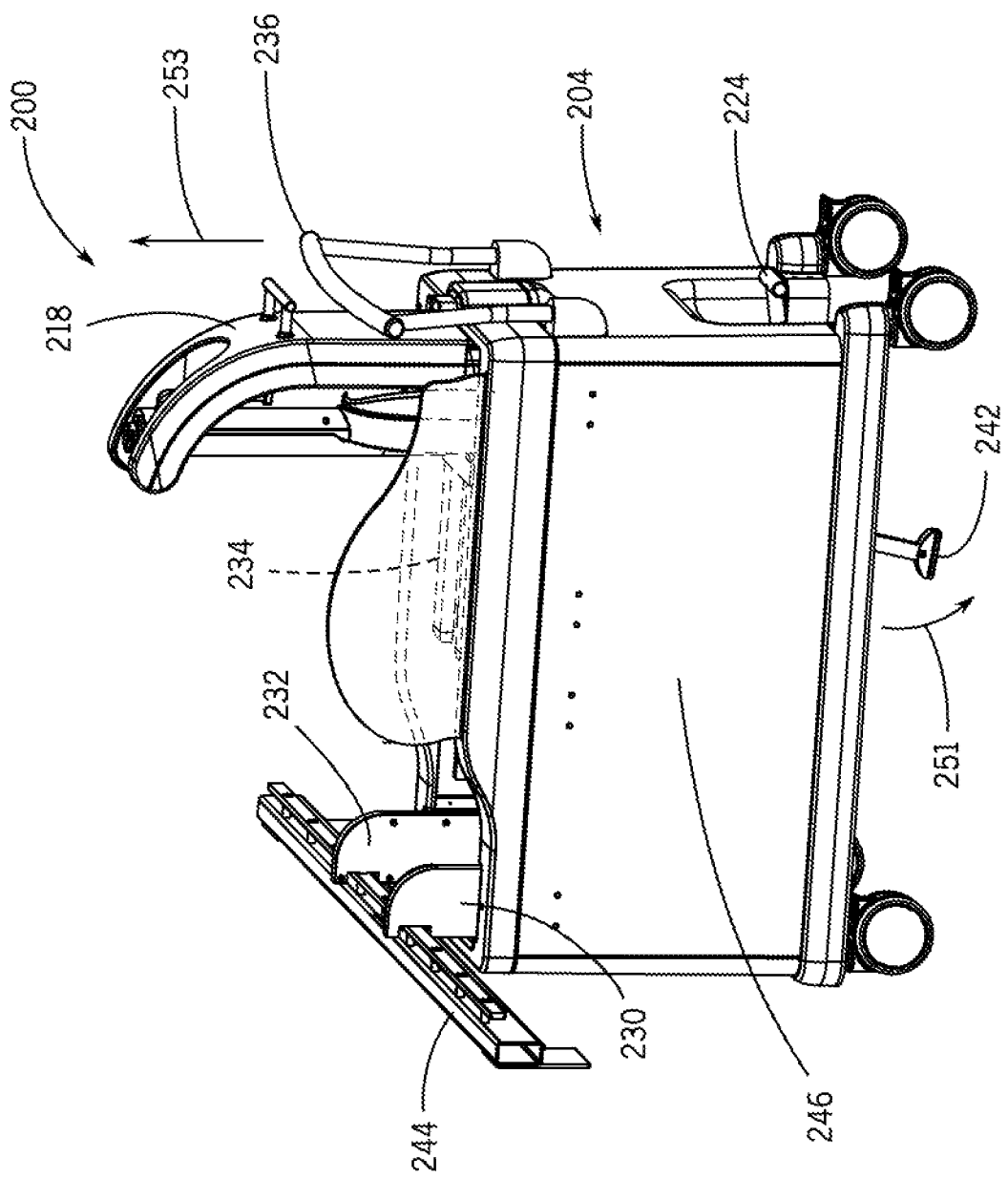
FIG. 5 is a perspective view of a mobile support system in a first position in accordance with an embodiment.
Figure 6:
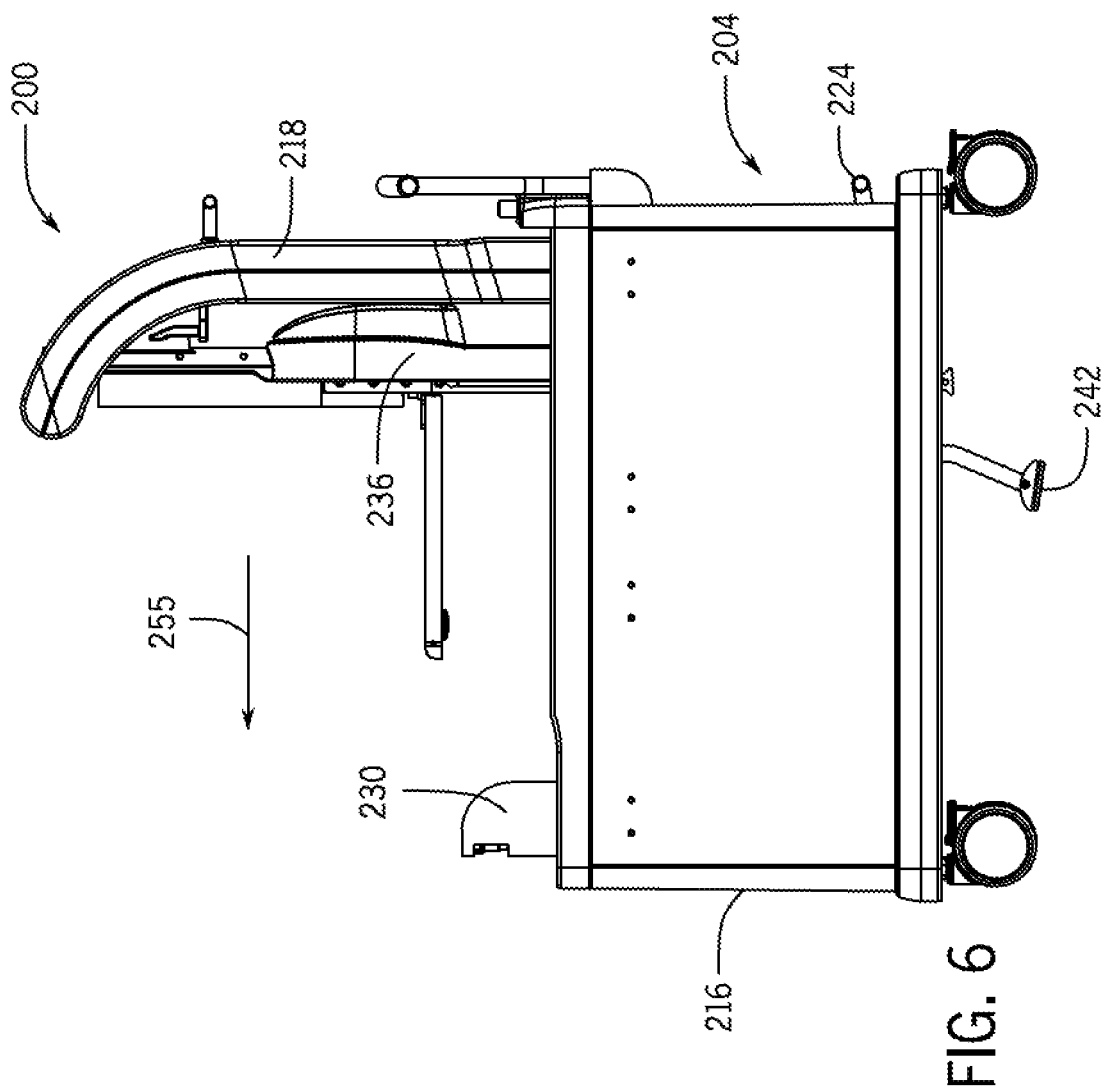
FIG. 6 is a perspective view of a mobile support system with a raised carriage at the first position in accordance with an embodiment.

To install the medical device on the rail of a bed or table, the mobile support 200 may be positioned next to the side of the bed adjacent to the rail on the table. FIG. 5 is a perspective view of a mobile support system in a first position in accordance with an embodiment. In FIG. 5, the mobile support 200 is wheeled up to the table so that the first rail detect guide 230 and the second rail detect guide 232 contact a rail 244 on the bed or table. For clarity, only the rail 244 of the bed or table is shown. The first rail detect guide 230 and the second rail detect guide 232 ensure that the table and rail 244 are in a correct height range. In addition, the first 230 and second 232 rail detect guides each include a link or switch that when actuated by contact with the rail 244 activate the mechanisms (e.g., hydraulics) used to raise and lower the carriage 234 (and thereby the support arm 218 and lower portion 236 of the medical device arm) so that the medical device may be installed onto the rail 244. In one embodiment, actuations of the links or switches in the first 230 and second 232 rail detect guides by contact with the rail 244 causes a bypass valve in a hydraulic circuit to close and switch the foot pedal 224 from a bypass mode to an actuation mode. In the bypass mode, the foot pedal 224 and mechanisms used to raise and lower the carriage 234 in the housing 204 of the mobile support 200 are inactive. In the actuation mode, the foot pedal 224 and the mechanisms used to raise and lower the carriage 234 are activated and a user may, for example, pump the foot pedal 224 to raise the carriage 234, support arm 218 and arm 236 upward in a vertical direction as indicated by arrow 253. A mechanism 246 may be used to raise the carriage 234 in response to the actuation of the foot pedal 224, for example, a scissor mechanism or lift as shown in FIG. 5. In various embodiments, the foot pedal 224 may be, for example, hydraulic or a mechanical linkage. In addition, actuation of the foot pedal 224 may cause the floor brake 242 to lower to contact the floor (as shown by arrow 251) and force or urge the mobile support 200 against the rail 244. FIG. 6 shows the carriage, support arm 218 and arm 236 in a raised position at the first position at the first end 214 of housing 204.

Figure 7:
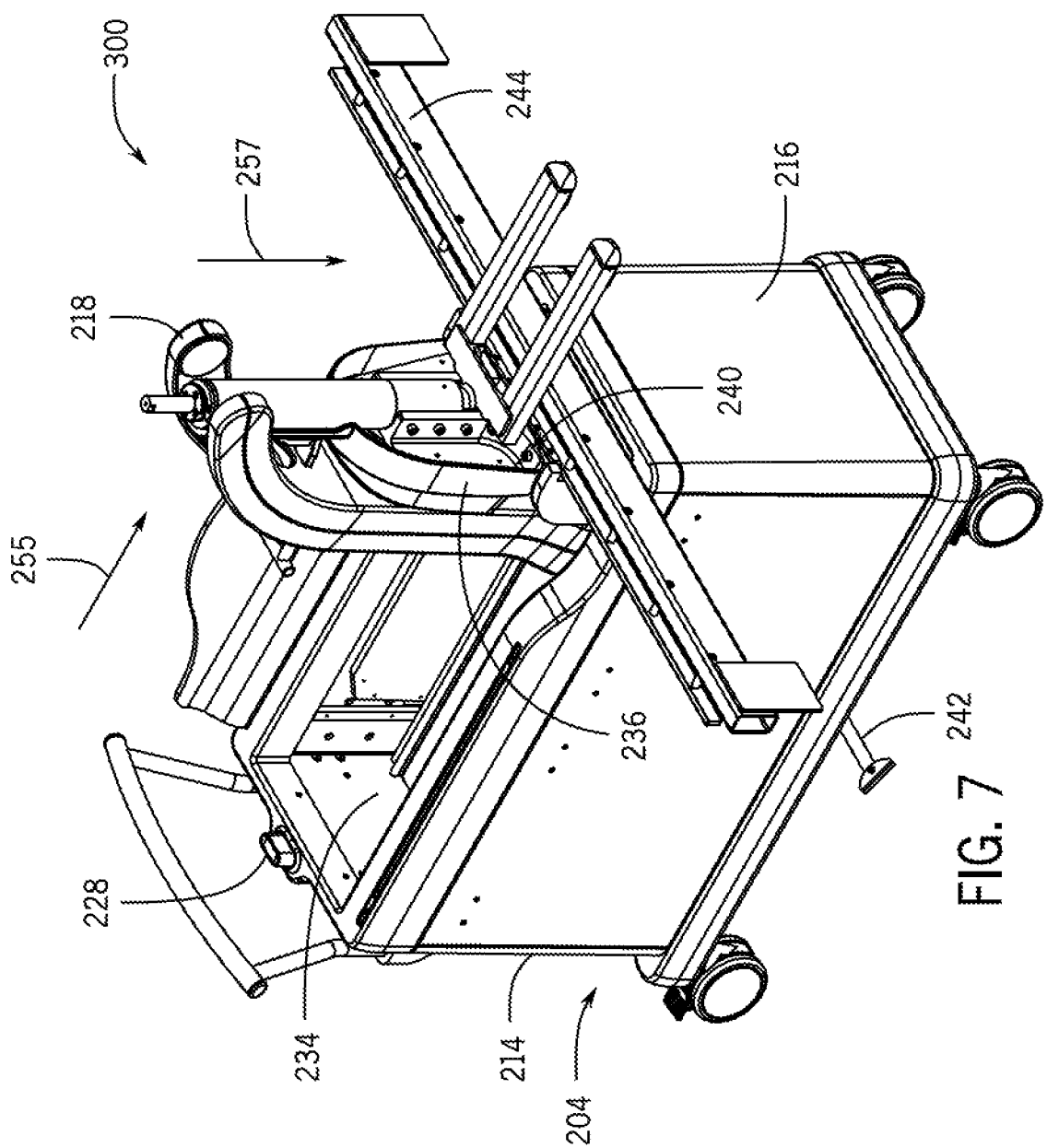
FIG. 7 is a perspective view of a mobile support system in a second position in accordance with an embodiment.
Figure 8:
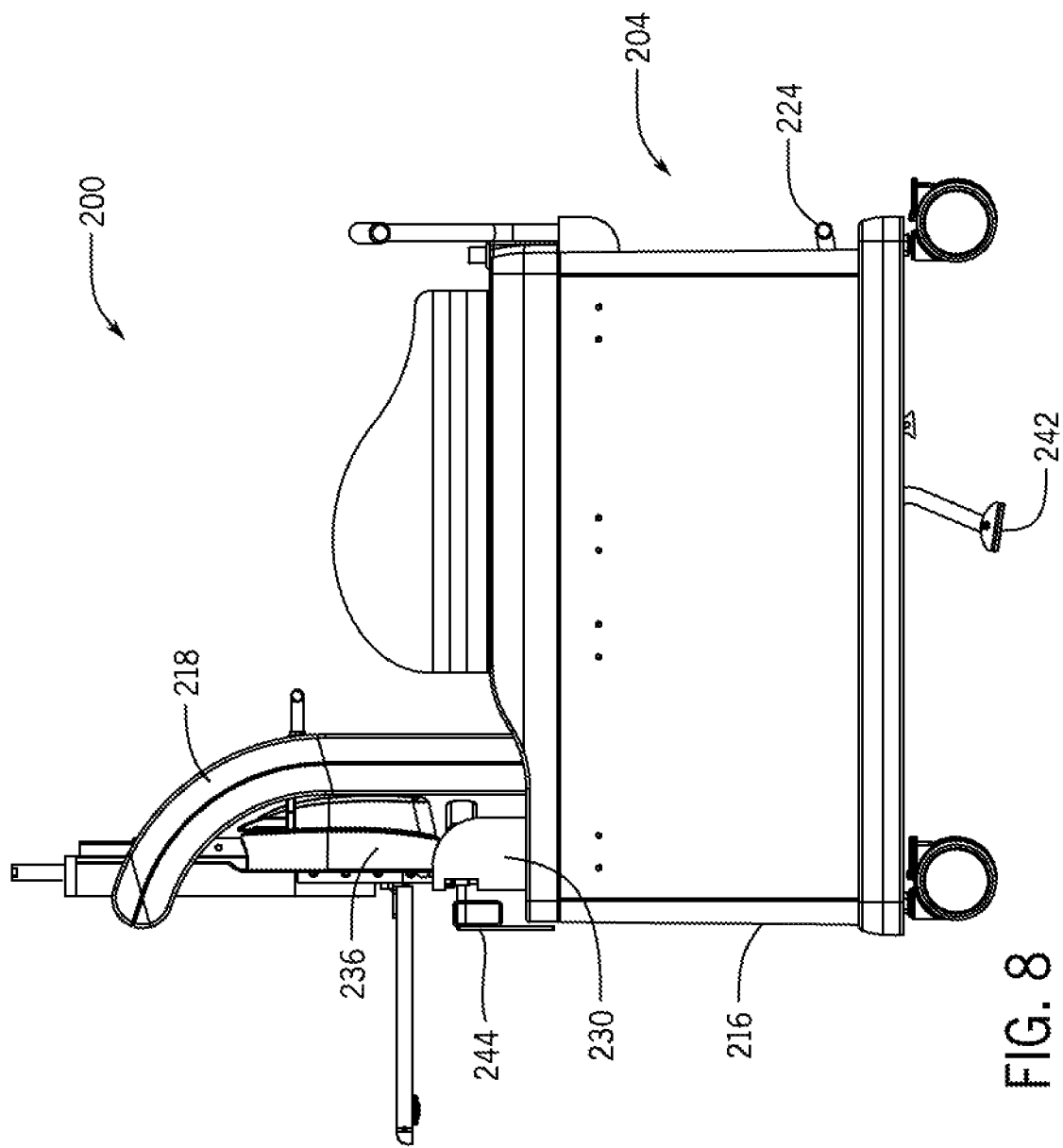
FIG. 8 is a perspective view of a mobile support system with a lowered carriage at the second position in accordance with an embodiment.

A user may then slide the support arm 218, arm 236 and carriage 234 from the first position proximate the first end 214 of the housing 204 to a second position as shown by arrow 255 in FIG. 6. FIG. 7 is a perspective view of a mobile support system in a second position in accordance with an embodiment. In FIG. 7, the support arm 218, arm 236 and carriage 234 have been moved in a horizontal direction (as shown by arrow 255) to the second position proximate the second end 216 of the housing 204. In one embodiment, the horizontal movement may be provided using linear bearings (not shown). A bias spring (not shown) may be used to push or force the carriage 234 towards the second position and hold the carriage 234 in the second position. In an embodiment, the bias spring may be implemented as an over center spring. In another embodiment, the bias spring may be implemented as a spring-loaded cam follower on a linear cam. The carriage 234, support arm 218 and arm 236 may then be lowered, for example, by actuating a button 228, towards the rail 244 (as shown by arrow 257) so that the arm 236 and base 240 are positioned on the rail 244. As mentioned above, a mechanism such as a scissor mechanism may be used to lower the carriage 234. When the base 240 is positioned and secured on the rail 244, the carriage 234 continues to be lowered downwards to disengage from the base 240 of the arm 236. FIG. 8 shows the carriage and support arm 218 is a lowered position in second position at the second end 216 of the housing 204. The mobile support 200 may then be wheeled away from the bed or table.

Figure 9:
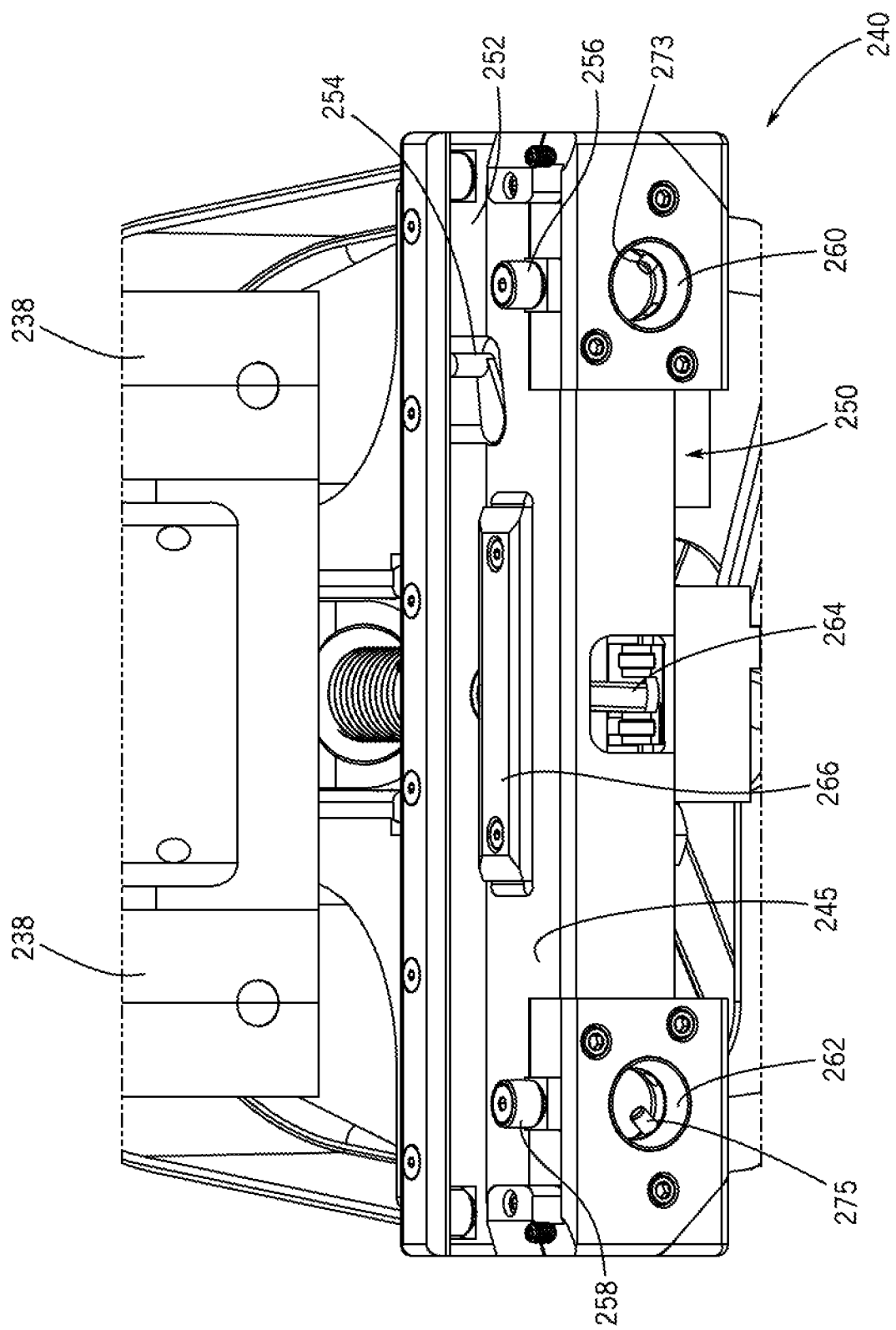
FIG. 9 is a perspective view looking upward towards a bottom portion of a base of an arm of a medical device in accordance with an embodiment.
Figure 10:
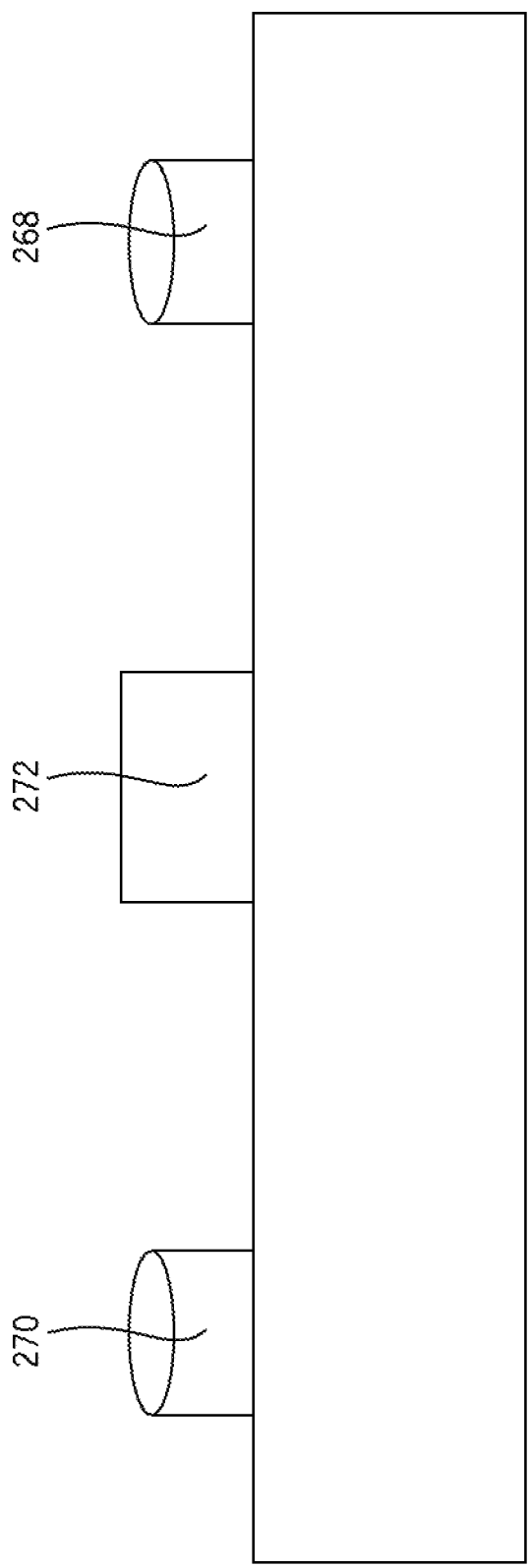
FIG. 10 is a side view of a mounting block in a carriage of a mobile support system in accordance with an embodiment.

It is desirable to keep the medical device locked onto the mobile support 200 until the arm 236 is properly seated on the rail 244 for installation on the rail 244 and that the medical device remains secured to the rail 244 until the mobile support 200 is properly positioned below the arm 236 for removal from the rail 244. As mentioned above, the base 240 of the arm 236 engages with the mounting block 241 on the mobile support 200. FIG. 9 is a perspective view looking upward towards a bottom portion of a base of an arm of a medical device in accordance with an embodiment and FIG. 10 is a side view of a mounting block in a carriage of a mobile support system in accordance with an embodiment. Referring to FIG. 9, base 240 includes a set of feet 238, a lip 252, a front side 245 and a bottom surface 250. A rail detect lever 254 is located on a bottom surface of lip 252. The rail detect lever 254 is used to make sure the arm base 240 is fully seated on the rail 244 (not shown) before the arm base 240 detaches from the mobile support 200. When the arm base 240 is lowered onto the rail, the rail detect lever 254 makes contact with the rail and either unlocks a first roller shaft 260 or a second roller shaft 262. In another embodiment, both the first roller shaft 260 and the second roller shaft 262 are locked and are unlocked when the rail detect lever 254 makes contact with the rail. When the base 240 and the mounting block 241 are engaged, a first pin 268 and a second pin 270 are positioned in the first roller shaft 260 and the second roller shaft 262, respectively. First pin 268 and second pin 270 are shown in FIG. 10 having a cylindrical or round shape, however, other shapes may be used for the pins 268 and 270. The first 268 and second 370 pins of the mounting block 241 are shown in FIG. 10. Referring again to FIG. 9, base 240 also includes a first roller 256 and a second roller 258 that are coupled to the first roller shaft 260 and the second roller shaft 262, respectively. When the base 240 and mounting block 241 are engaged, the first roller 256 and the second roller 258 are in a position (not shown in FIG. 9) so they lie substantially parallel to the first side 245 of the base 240 and do not protrude outward from and perpendicular to the first side 245 of the base 240. Once the first 260 and second 262 roller shafts are unlocked, the mobile support 200 can continue to be lowered so as to disengage the first 268 and second 270 pin of the mounting block 241 from base 240. As the pin 268 is removed, a follower pin 273 in first roller shaft 260 rotates the roller shaft 260 to move the first roller 256 to a position (shown in FIG. 9) where it protrudes outward from and perpendicular to the first side 245 of base 240 so that the first roller 256 lies under the rail (not shown). As the pin 270 is removed, a follower pin 275 in second roller shaft 262 rotates the roller shaft 262 to move the second roller 258 to a position (shown in FIG. 9) where it protrudes outward from and perpendicular to the first side 245 of base 240 so that the second roller 258 lies under the rail (not shown). First roller 256 and second roller 258 secure or lock the base 240 onto the rail. When pins 268 and 270 disengage from the roller shafts 260 and 262 respectively, the follower pins 273 and 275 slide inwards and engage a locking mechanism that prevents roller shafts 260 and 262 from rotating.

Figure 11:
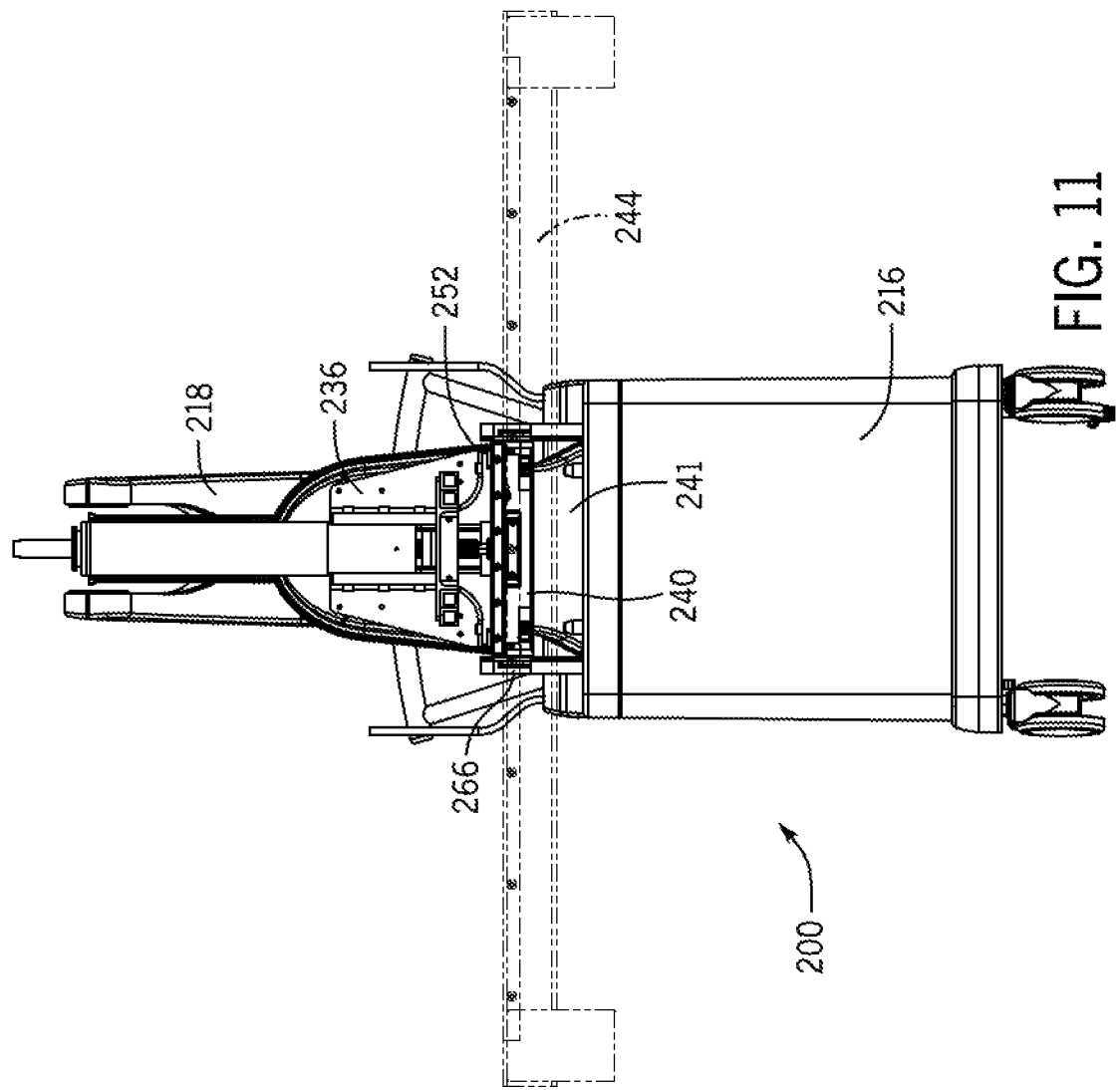
FIG. 11 is a front view of a mobile support system in accordance with an embodiment.

Base 240 also includes a friction brake 266 positioned on the first side 245 of the base 240 and a brake release 264 positioned in the bottom surface 250 of the base 240. When the base 240 and mounting block 241 (shown in FIG. 10) are engaged, a brake release pin 272 (shown in FIG. 10) on the mounting block 241 is positioned in the brake release 264. Brake release pin 272 is shown in FIG. 10 having a rectangular shape, however, other shapes may be used for the brake release pin 272. As the brake release pin 272 is removed from the brake release as the mobile support 200 is lowered, the brake 266 is applied and forced against the rail (e.g., a spring-loaded brake) to secure the base 240 to the rail as shown in FIG. 11. FIG. 11 is a front view of a mobile support system in accordance with an embodiment. The support arm 218 and arm 236 are in the second position proximate to the second end 216 of the mobile support 200. The base 240 of the arm 236 is seated on the rail 244 and the brake 266 is against the rail 244. As the carriage 234 is lowered, the floor brake 242 is released and raises up from the floor. Once the carriage 234 of the mobile support 200 is lowered to disengage the mounting block 241 from the base 240, the mobile support 200 may then be wheeled away from the bed or table. The medical device mounted to the table is shown in FIG. 1.

Figure 12:
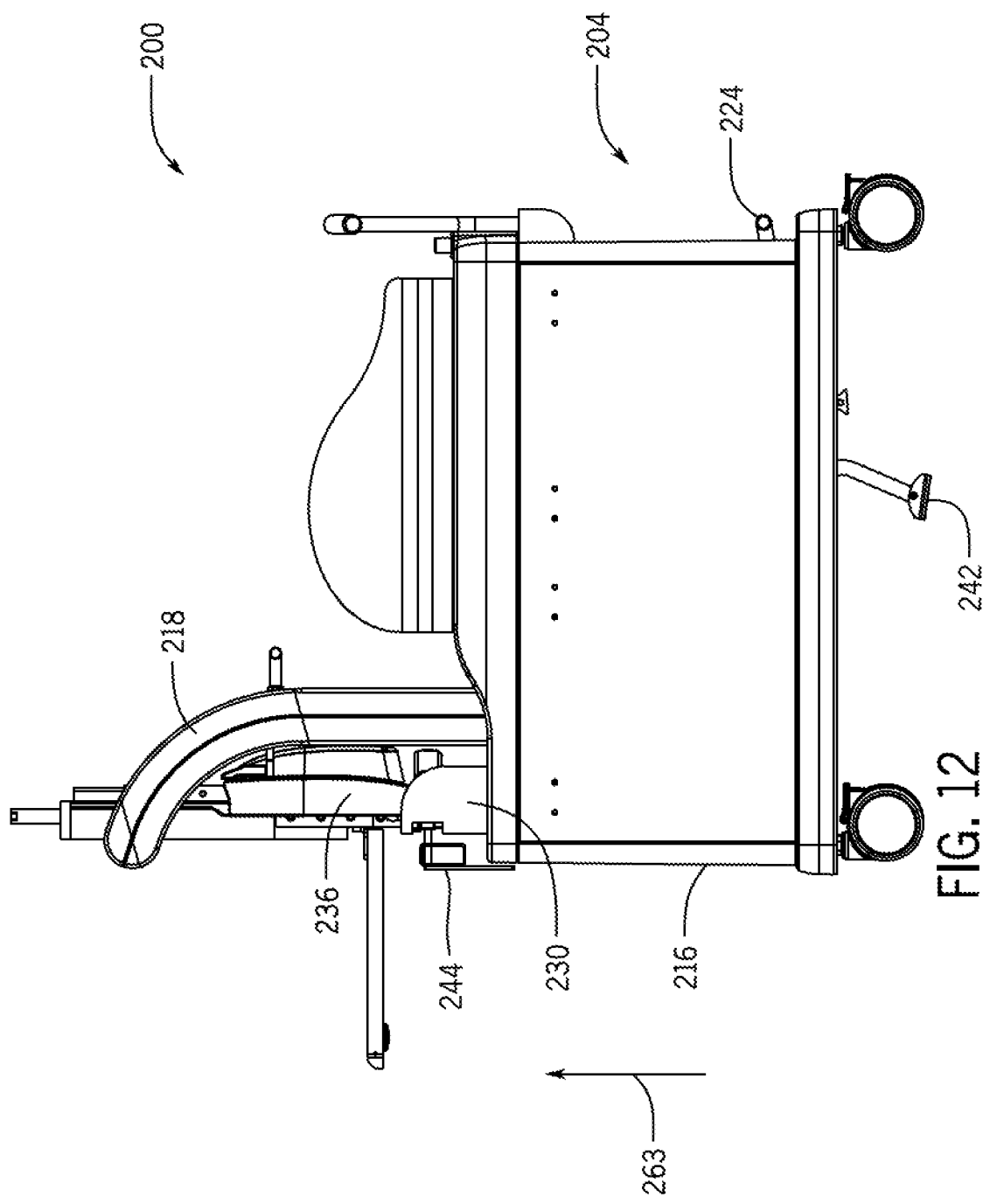
FIG. 12 is a perspective view of a mobile support system with a lowered carriage at the second position in accordance with an embodiment.
Figure 13:
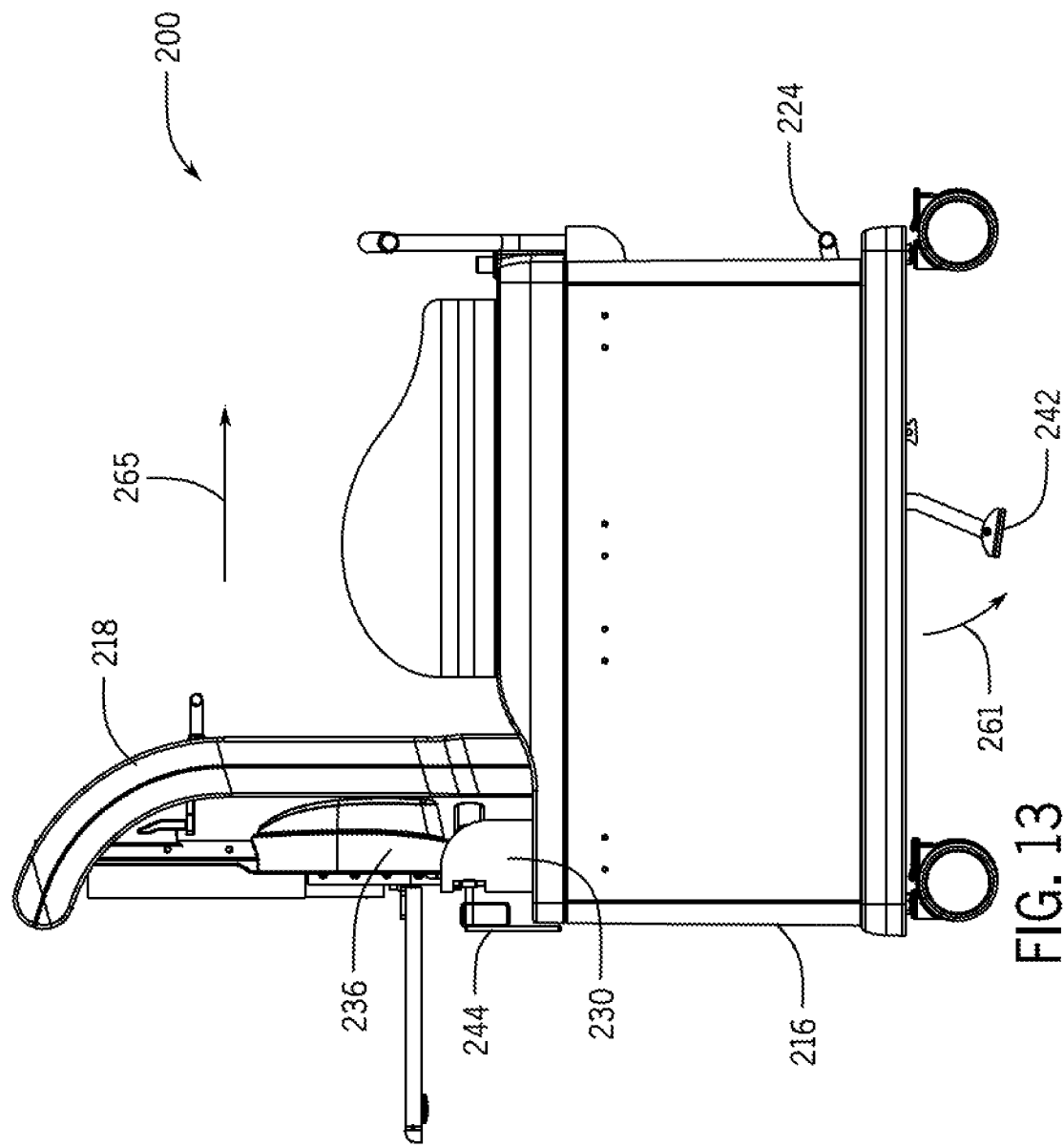
FIG. 13 is a perspective view of a mobile support system in a second position in accordance with an embodiment.

To remove the medical device from the rail of a bed or table, the mobile support 200 may be positioned next to the side of the bed adjacent to the rail on the table. FIG. 12 is a perspective view of a mobile support system with a lowered carriage in the second position and FIG. 13 is a perspective view of a mobile support system with a raised carriage in the second position. Referring to FIGS. 12 and 13, the mobile support 200 is wheeled up to the table so that the first rail detect guide 230 and the second rail detect guide 232 contact the rail 244 on the bed or table. For clarity, only the rail 244 of the bed or table is shown. As discussed above with respect to FIG. 5, the first 230 and second 232 rail detect guides each include a link or switch that when actuated by contact with the rail 244 unlock the mechanisms (e.g., hydraulics) used to raise and lower the carriage 234 (and thereby the support arm 218 and lower portion 236 of the medical device arm) so that the medical device may be removed from the rail 244. Once the foot pedal 224 and the mechanisms used to raise and lower the carriage 234 are unlocked, a user may, for example, pump the foot pedal 224 to raise the carriage 234, support arm 218 and arm 236 upward in a vertical direction as indicated by arrow 263. In addition, actuation of the foot pedal 224 causes the floor brake to lower to contact the floor (as shown by arrow 261) and force or urge the mobile support 200 against the rail 244. As the carriage 234 is raised, the mounting block 241 on the mobile support 200 engages the base 240 of the arm 236.

Referring again to FIGS. 9 and 10, when the base 240 and the mounting block 241 are engaged, a first pin 268 and a second pin 270 are positioned in the first roller shaft 260 and the second roller shaft 262, respectively. As the first pin 268 is inserted into the first roller shaft 260, the follower pin 273 in first roller shaft 260 first unlocks the roller shaft 260 and then rotates the roller shaft 260 to move the first roller 256 to a position (not shown in FIG. 9) so it lies substantially parallel to the first side 245 of the base 240 and does not protrude outward from and perpendicular to the first side 245 of the base 240. As the second pin 270 is inserted into the second roller shaft 262, the follower pin 275 in second roller shaft 262 first unlocks the roller shaft 262 and then rotates the roller shaft 262 to move the second roller 258 to a position (not shown in FIG. 9) so it lies substantially parallel to the first side 245 of the base 240 and does not protrude outward from and perpendicular to the first side 245 of the base 240. In addition, as the base 240 and mounting block 241 are engaged, the brake release pin 272 (shown in FIG. 10) on the mounting block 241 is positioned in the brake release 264. As the brake release pin 272 is inserted in the brake release 264 as the mobile support 200 is raised, the brake 266 is released and no longer applies a force to the rail 244. In an embodiment, the brake release pin 272 makes contact with a rocker in brake release 264 and the rocker may be attached to the brake with a tie rod. Once the base 240 and the mounting block 241 are engaged, the roller shafts 260, 262 are unlocked, rollers 256, 258 are rotated out of the position underneath the rail and the brake is released. As the arm base 240 is raised off of the rail the rail detect lever 254 disengages from the rail (e.g., no longer makes contact with the rail) and at least one of the first roller shaft 260 and the second roller shaft 262 are locked.

Figure 14:
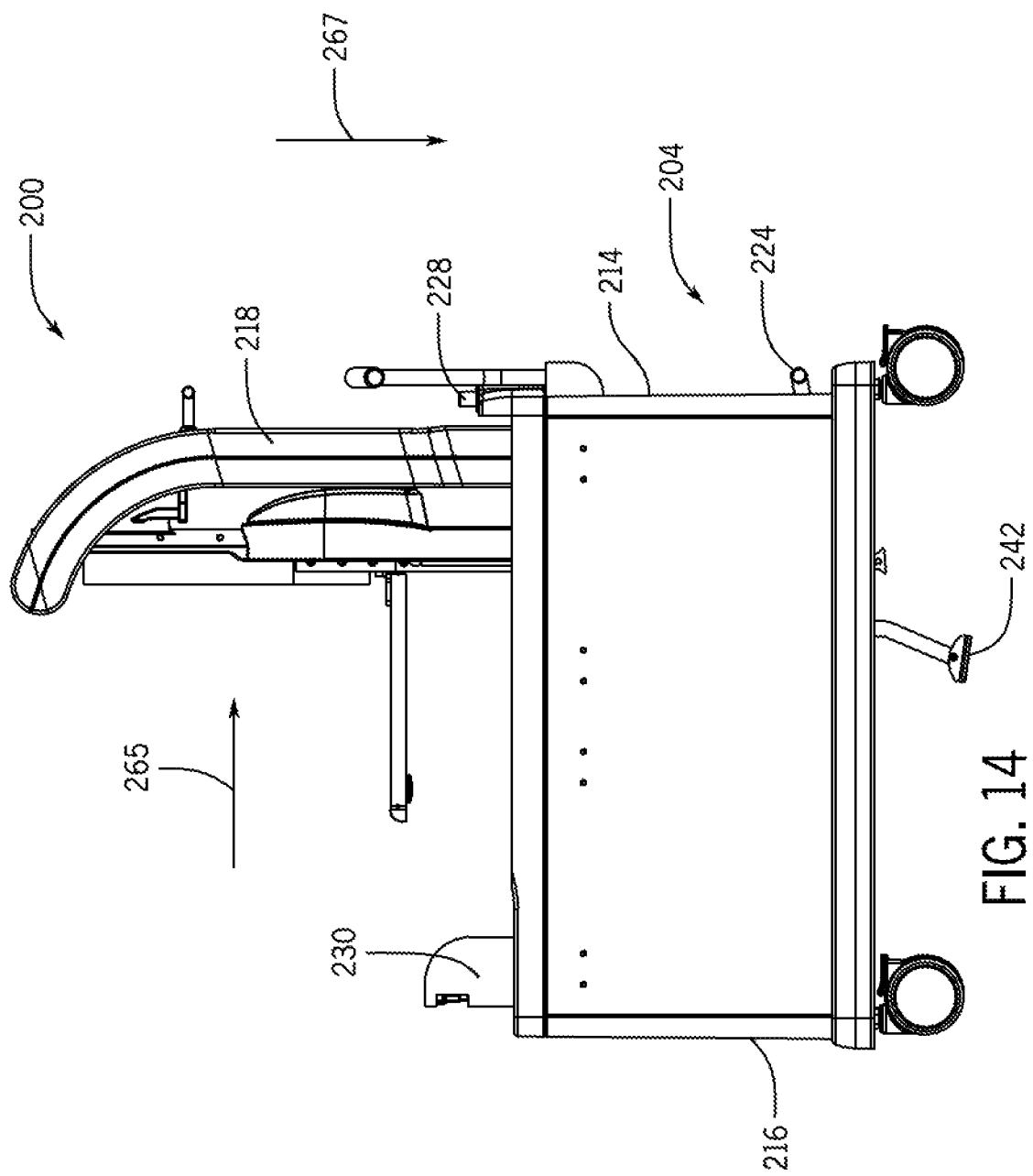
FIG. 14 is a perspective view of a mobile support system with a raised carriage at the first position in accordance with an embodiment.

Returning to FIG. 13, the carriage 234 of mobile support 200 may then continue to be raised until the arm 236 and support arm 218 are a sufficient distance above the table. A user may then slide (as shown by arrow 265) the support arm 218, arm 236 and carriage 234 from the second position proximate the second end 216 of the housing 204 to a first position as shown in FIG. 14. FIG. 14 is a perspective view of a mobile support system with a raised carriage at the first position in accordance with an embodiment. In FIG. 14, the support arm 218, arm 236 and carriage 234 have been moved in a horizontal direction (as shown by arrow 265) to the first position proximate the first end 214 of the housing 204. In one embodiment, the horizontal movement may be provided using linear bearings (not shown). The carriage 234, support arm 218 and arm 236 may then be lowered (as shown by arrow 267), for example, by actuating a button 228, into the housing so that the arm 236 and base 240 are in a storage position as shown in FIG. 15. As mentioned above, a mechanism such as a scissor mechanism may be used to lower the carriage 234. Referring to FIG. 15, when the support arm 218 and arm 236 are in the storage position, the floor brake 242 releases and moves to a raised position (as shown by arrow 269). The mobile support 200 may then be wheeled away from the bed or table.

This written description used examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims. The order and sequence of any process or method steps may be varied or re-sequenced according to alternative embodiments.

Many other changes and modifications may be made to the present invention without departing from the spirit thereof. The scope of these and other changes will become apparent from the appended claims.

What is claimed is:

1. A mobile support system for a medical device having an arm with a base, the mobile support system comprising:
   a body comprising a housing having a top surface, a first end and a second end and a carriage positioned within the housing;
   a mechanism coupled to the carriage and configured to cause movement of the carriage;
   a set of wheels coupled to the housing;
   a support arm coupled to the carriage and extending vertically upward from the top surface of the housing, the support arm configured to support the arm of the medical device;
   a mounting block coupled to the carriage proximate to the support arm, the mounting block configured to couple with the base of the arm of the medical device;
   a first rail detect guide located on the top surface at the second end of the housing; and
   a second rail detect guide located on the top surface at the second end of the housing;
   wherein the first rail detect guide and the second rail detect guide are configured to unlock the mechanism used to cause movement of the carriage when contact is made between the first rail detect guide and the second rail detect guide and a surface.

2. The mobile support system according to claim 1, further comprising a floor brake coupled to the housing.

3. The mobile support system according to claim 2, further comprising a foot pedal coupled to the mechanism configured to cause movement of the carriage and the floor brake.

4. The mobile support system according to claim 1, wherein the surface is a surface of a rail of a table.

5. The mobile support system according to claim 1, wherein the first rail detect guide includes a mechanical link that opens a bypass valve when the mechanical link is actuated.

6. The mobile support system according to claim 1, wherein the second rail detect guide includes a mechanical link that opens a bypass valve when the mechanical link is actuated.

7. The mobile support system according to claim 1, wherein the mechanism configured to cause movement of the carriage is a scissor mechanism.

8. The mobile support system according to claim 1, wherein the support arm and mounting block are configured to move within the carriage between a first position proximate the first end of the housing and a second position proximate the second end of the housing.

9. The mobile support system according to claim 8, further comprising a bias spring configured to apply a force on the carriage when the carriage is at the second position.

10. A mobile support system for a medical device having an arm with a base, the mobile support system comprising:
 a body comprising a housing having a top surface and a carriage positioned within the housing;
 a mechanism coupled to the carriage and configured to cause movement of the carriage;
 a set of wheels coupled to the housing;
 a floor brake coupled to the housing, the floor brake configured to be actuated in response to movement of the carriage;
 a support arm coupled to the carriage and extending vertically upward from the top surface of the housing, the support arm configured to support the arm of the medical device; and
 a mounting block coupled to the carriage proximate to the support arm, the mounting block configured to couple with the base of the arm of the medical device.

11. The mobile support system according to claim 10, further comprising:
 a first rail detect guide located on the top surface at an end of the housing; and
 a second rail detect guide located on the top surface at a second end of the housing;
 wherein the first rail detect guide and the second rail detect guide are configured to unlock the mechanism used to cause movement of the carriage when contact is made between the first rail detect guide and the second rail detect guide and a surface.

12. The mobile support system according to claim 11, wherein the surface is a surface of a rail of a table.

13. The mobile support system according to claim 10, further comprising a foot pedal coupled to the mechanism configured to cause movement of the carriage and the floor brake.

14. The mobile support system according to claim 10, wherein the support arm and mounting block are configured to move within the carriage between a first position proximate the first end of the housing and a second position proximate the second end of the housing.

15. The mobile support system according to claim 14, further comprising a bias spring configured to apply a force on the carriage when the carriage is at the second position.

16. A mobile support system comprising:
 a medical device having an arm with a base, the base comprising a rail detect lever configured to be actuated when contact is made between the rail detect lever and a surface;
 a body comprising a housing and a carriage positioned within the housing;
 a support arm coupled to the carriage and extending vertically upward from the housing, the support arm configured to support the arm of the medical device; and
 a mounting block coupled to the carriage proximate to the support arm, the mounting block configured to couple with the base of the arm of the medical device.

17. The mobile support system according to claim 16, wherein the surface is a surface of a rail of a table.

18. The mobile support system according to claim 17, wherein the base of the arm of the medical device further comprises at least one roller shaft configured to be unlocked when the rail detect lever is actuated.

19. A mobile support system comprising:
 a medical device having an arm with a base, the base comprising a brake and a brake release coupled to the brake;
 a body comprising a housing and a carriage positioned within the housing;
 a support arm coupled to the carriage and extending vertically upward from the housing, the support arm configured to support the arm of the medical device; and
 a mounting block coupled to the carriage proximate to the support arm, the mounting block configured to couple with the base of the arm of the medical device, the mounting block configured to actuate the brake release when the mounting block engages the base of the arm.

20. The mobile support system according to claim 19, wherein when the mounting block actuates the brake release, the brake is deactivated.

21. A mobile support system comprising:
 a medical device having an arm with a base, the base comprising:
  a first roller;
  a first roller shaft coupled to the first roller;
  a first locking mechanism coupled to the first roller shaft;
  a second roller;
  a second roller shaft coupled to the second roller; and
  a second locking mechanism coupled to the second roller shaft;
 a body comprising a housing and a carriage positioned within the housing;
 a support arm coupled to the carriage and extending vertically upward from the housing, the support arm configured to support the arm of the medical device; and
 a mounting block coupled to the carriage proximate to the support arm, the mounting block configured to couple with the base of the arm of the medical device, the mounting block comprising a set of pins configured to couple with the first roller shaft and the second roller shaft, wherein the first locking mechanism and the second locking mechanism are configured to lock the first roller shaft and the second roller shaft, respectively, when the set of pins of the mounting block are disengaged from the first roller shaft and the second roller shaft.

22. The mobile support system according to claim 21, wherein the first locking mechanism and the second locking mechanism are configured to unlock the first roller shaft and the second roller shaft, respectively, when the set of pins of the mounting block are engaged with the first roller shaft and the second roller shaft.

23. The mobile support system according to claim 21, wherein the first locking mechanism comprises a follower pin disposed within the first roller shaft.

24. The mobile support system according to claim 21, wherein the second locking mechanism comprises a follower pin disposed within the second roller shaft.

25. The mobile support system according to claim 22, wherein the first roller and the second roller are configured to move from a first position to a second position when the set o pins of the mounting block are engaged with the first roller shaft and the second roller shaft.

* * * * *